United States Patent [19]

Bruce

[11] Patent Number: 5,980,540
[45] Date of Patent: Nov. 9, 1999

[54] PERFORATED COVER FOR COVERING SPACES IN THE CRANIUM AND CONFORMING TO THE SHAPE OF THE CRANIUM

[75] Inventor: Robert Bruce, Ventura, Calif.

[73] Assignee: Kinamed, Inc., Newbury Park, Calif.

[21] Appl. No.: 08/834,056

[22] Filed: Apr. 11, 1997

[51] Int. Cl.$^6$ .................................................. A61B 17/08
[52] U.S. Cl. .......................... 606/151; 606/69; 606/60; 606/70
[58] Field of Search .............................. 606/151, 69, 60, 606/70; 128/92; 623/16

[56] References Cited

U.S. PATENT DOCUMENTS

| | | | |
|---|---|---|---|
| 5,372,598 | 12/1994 | Luhr et al. | 606/69 |
| 5,380,328 | 1/1995 | Morgan | 606/70 |
| 5,468,242 | 11/1995 | Reisberg | 606/69 |
| 5,766,176 | 6/1998 | Duncan | 606/69 |

OTHER PUBLICATIONS

The Definitive Neuro Fixation System; Anspach Fixation Systems (Brochure).

Primary Examiner—Michael Buiz
Assistant Examiner—Vy Quang Bui
Attorney, Agent, or Firm—Oppenheimer Wolff & Donnelly LLP

[57] ABSTRACT

The cranial cover can form a contoured surface to conform to a patient's cranium. The cover is an array of generally evenly spaced screw-receiving openings. Arms extend between the screw-receiving openings from one screw-receiving opening to the adjacent screw-receiving openings. The centerline of each arm is angled to the center of the screw-receiving openings between which the arm extends. The four arms of four adjacent screw-receiving openings create a rhombus shaped central opening.

1 Claim, 2 Drawing Sheets

PERFORATED COVER FOR COVERING SPACES IN THE CRANIUM AND CONFORMING TO THE SHAPE OF THE CRANIUM

TECHNICAL FIELD

The present invention relates in general to an improved perforated cover used to repair gaps in the cranium.

BACKGROUND OF THE INVENTION

Surgeons sometimes face the need to reconstruct large defects in the cranium. These defects result from bone loss due to tumor resection, osteomyelitis or trauma. The surgical goal is to cover the area of missing bone to provide mechanical protection for the brain. At the same time, the cover shall restore the normal aesthetic contours of the skull.

Mesh cover plates of titanium or other biocompatible materials are often used. Typically, the mesh has an array of spaced surgical screw-receiving openings with a mesh of arms connecting adjacent openings. A surgeon takes a sheet of this material and trims it to the desired size. After attempting to bend the mesh to conform as closely as possible to the pre-existing cranial shape, the surgeon fastens the mesh to existing bone through the screw-receiving openings at the periphery of the material.

Surgeons encounter one difficulty when using these metal meshes—shaping the mesh to match the anatomical contours of the skull. Because of their construction, the meshes do not readily allow such contouring. The arms interconnecting the openings in prior art meshes are perpendicular to each other and aligned with the centers of the openings. As the material is bent into a spherical shape, the distance between the screw-receiving openings must change slightly. The perpendicular arms do not readily permit the distance to change. More specifically, as the mesh is bent into a more spherical shape, the distance between openings must increase in the more central portion of the mesh and decrease in the peripheral portions of the mesh panel. Therefore, it is very difficult to contour the material to the degree necessary to match the contours existing in human craniums.

Therefore it would be highly desirable to have a new and improved cranial bone plate cover that readily allows the cover to be contoured into a desired configuration and to hold the contoured shape. There have been attempts at changing the design of the mesh. In a mesh sold by Leibinger, the arms connecting the screw-receiving openings have bends as shown in FIG. 1. Though this may be an improvement over the earlier meshes in terms of its ability to achieve spherical contours, the design is less than ideal. The mesh does not hold its shape very well, which permits the mesh to be deformed further after it has been surgically implanted.

SUMMARY OF THE INVENTION

Therefore, the principal object of the present invention is to provide a new and improved cranial cover that readily allows the cover to be contoured into a desired configuration.

The present invention accomplishes that object with an array of evenly spaced screw-receiving openings. Each arm may be wider near its two screw-receiving openings and narrower near the arm's center. Arms extend between the screw-receiving openings from one screw-receiving opening to the adjacent screw-receiving openings. Each opening has a center, and each arm has a centerline. The centerline of each arm is angled to the common center of the adjacent screw-receiving openings between which the arm extends. Further, the four angled arms' centerlines adjacent a given screw-receiving opening are all angled relative to the same extent and direction. When viewed from the top, the space between four adjacent arms and openings is a rhombus in with the apexes are off-set from the openings.

DETAILED DESCRIPTION OF THE PREFERRED EMBODIMENTS:

Cranial bone plate or cover 10 (FIGS. 2–4) is constructed in accordance with the present invention. The cranial bone cover 10 can be laid over a large cranial defect 11 caused by trauma, tumor or other disease. The cover is then attached to adjacent, intact cranial bone structure 14 (FIG. 3) to provide a relatively smooth contoured, cosmetically pleasing, cranial bone cover. In this regard, the cranial bone cover 10 is sufficiently flexible to curve to simulate the curvature of the cranium.

Figure 1:
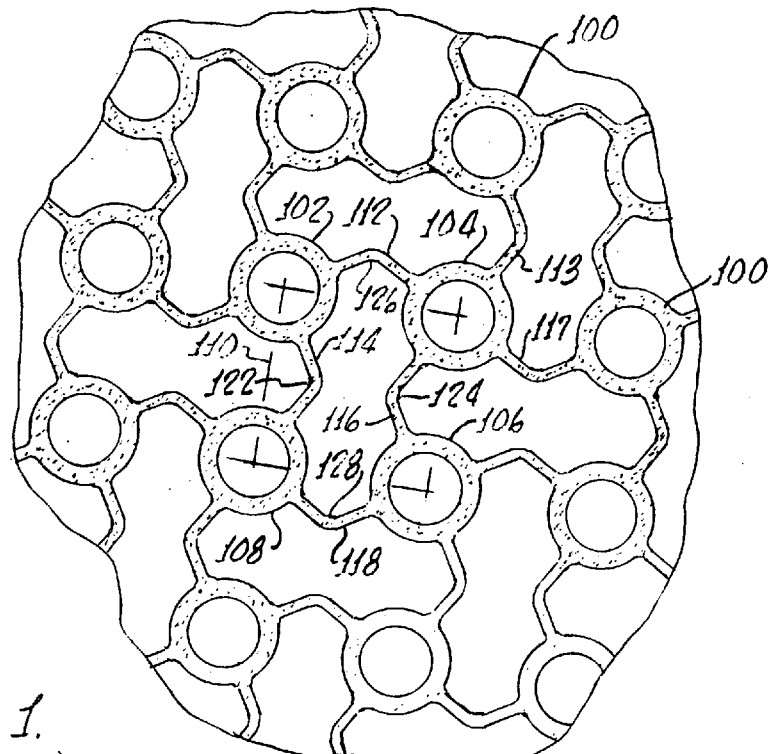
FIG. 1 is a plan view of a prior art cranial mesh.

Before describing the cover in greater detail, applicant will first explain the prior art. FIG. 1 shows the Leibinger Dynamic Mesh, which is prior art. There, screw openings 100 form a grid. First, focus on four adjacent openings 102, 104, 106 and 108 that form an imaginary square or rectangle 110 in space. Angled connecting arms 112, 114, 116 and 118 connect the openings. Opposite vertices 122 and 124 of arms 114 and 116 point toward each other, but the other set of opposite vertices 126 and 128 of arms 112 and 118 point away from each other. Furthermore, if one focuses on any one opening, e.g., opening 104, the portions of the arms 112, 113, 116 and 117 intersecting opening 104 do so perpendicular to the opening and at 90° intervals. Thus, half of opposite arms 112 and 117 are aligned with each other. Arms 113 and 116 have a similar arrangement.

Figure 3:
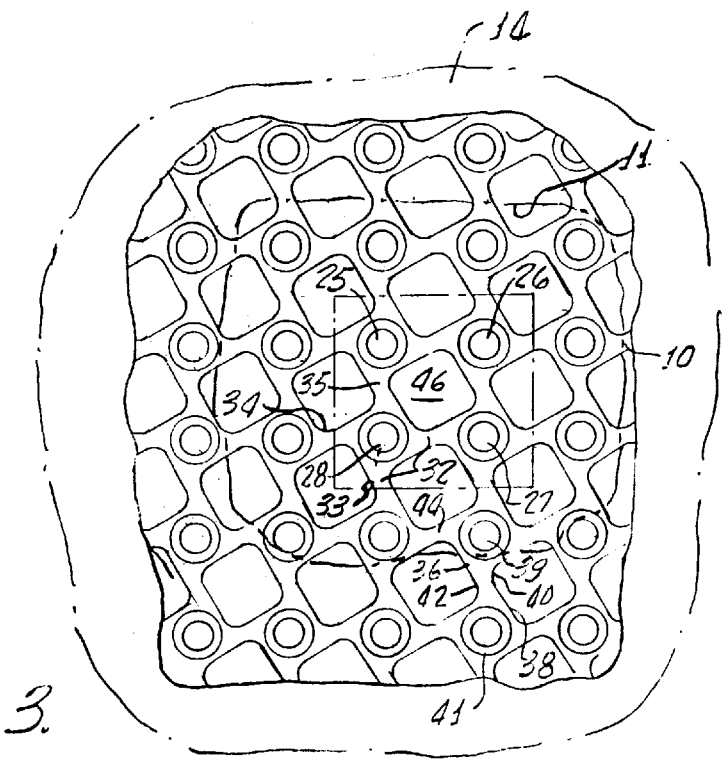
FIG. 3 is an enlarged, top plan view of part of the cranial mesh of FIG. 2 covering a cranial defect.
Figure 2:
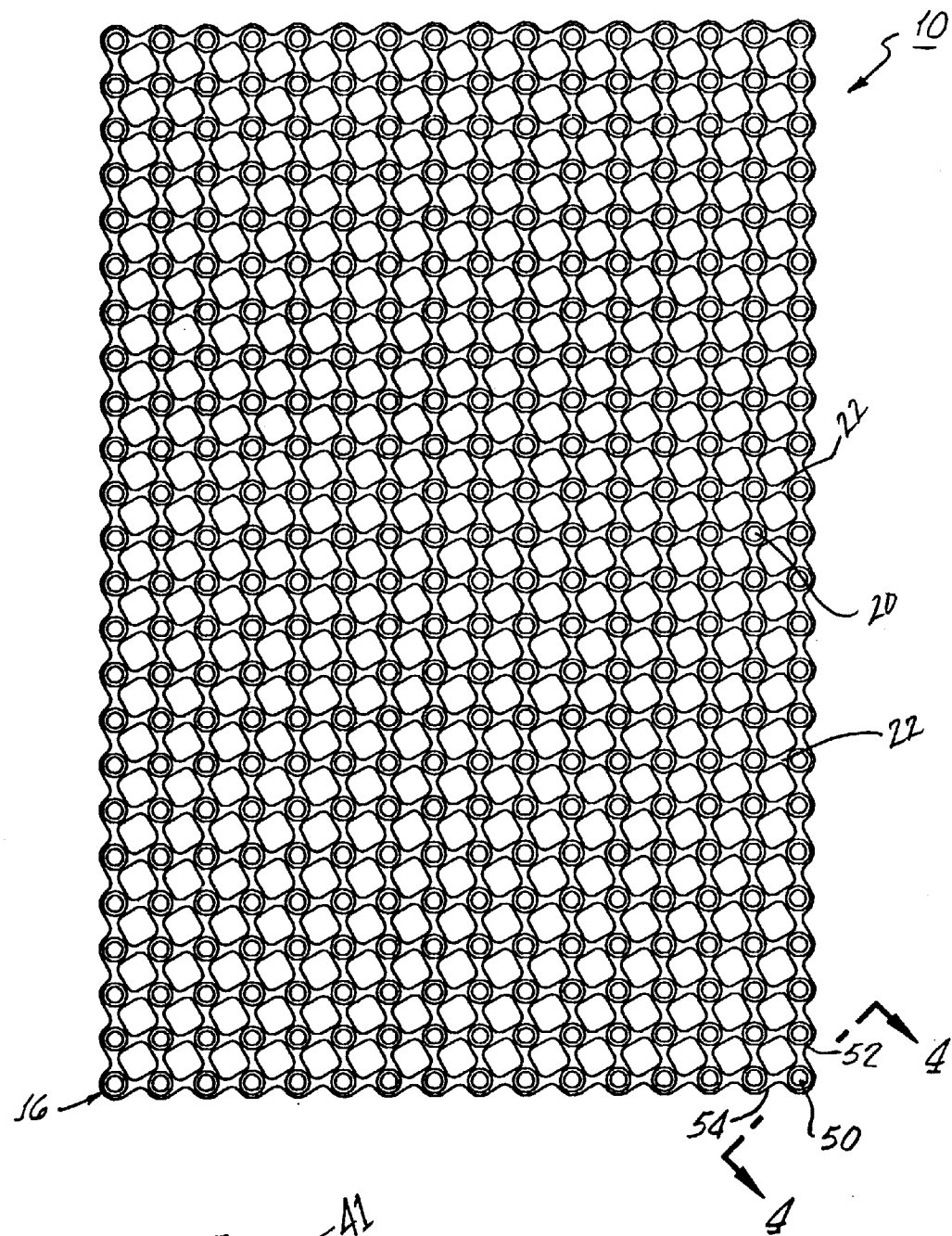
FIG. 2 is a plan view of a cranial mesh that is constructed in accordance with the present invention.

Returning to the present invention, cover 10 also has an array of screw-receiving openings 20 connected by arms 22 (FIGS. 2 and 3). In the exemplary embodiment, cover 10 is a 24×16 opening array, which forms a 90×135 mm array. Other sizes also would be acceptable. Titanium is the preferred material for the cover 10 because of its resistance to corrosion. Titanium is also very malleable.

Figure 4:
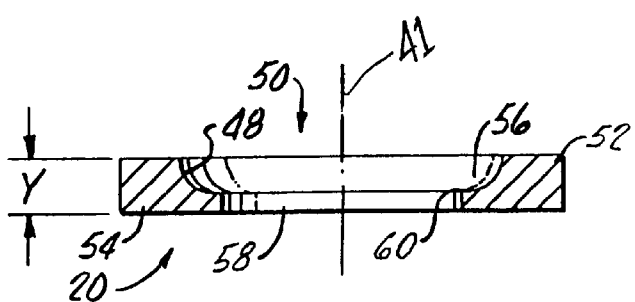
FIG. 4 is a cross-sectional view of the cranial mesh of FIG. 2 taken substantially through plane 4—4 of FIG. 2.

As FIG. 4 shows, the cranial bone cover 10 has a low profile thickness (dimension Y) of about 0.4 mm. That thickness allows the mesh to be sufficiently strong but malleable. Also, when the cranial bone cover 10 is sandwiched between the patient's cranium and scalp, it is thin enough that it does not create a large bulge. This is especially important if the cover is over an area without hair.

One way to visualize the mesh is to consider each set of four adjacent openings and their four connecting arms to be a single subsection 24 (FIG. 3). Subsection 24, which is within the dashed lines in FIG. 3, contains four screw-receiving openings 25–28. Arms extend from each screw-receiving opening 25–28. The exemplary embodiment employs four arms equally spaced about each opening. Thus, for opening 28, for example, arms 32–35 project from that opening (FIG. 3). Though the exemplary embodiment has four arms per opening, one could use different numbers. Some configurations may allow insufficient flexibility, however.

Each arm is wider adjacent its screw-receiving openings and narrower between the openings. As FIG. 3 shows, arm 36 (chosen to avoid interfering with the reference numerals for arms 32–35), has wider portions 38 and 40 near their respective openings 39 and 41. Arm also has a narrower portion 42 between the wider portions.

The centerline of each arm 32–35 is angled relative to a line connecting the centers of adjacent screw-receiving openings between which the arm extends. In FIG. 3, arm 70 has a centerline 72. FIG. 3 shows the centerline drawn with extensions beyond the adjacent openings 75 and 76. Openings 75 and 76 also have a line 74 connecting the centers of the adjacent openings. As FIG. 3 shows, centerline 72 is angled with respect to line 74. Further, the centerlines of the four angled arms 32–35 adjacent a given screw-receiving opening 28 are all angled to the same extent and direction. Also, the shape of each arm including its narrow center creates relatively large spaces such as space 46 in each subsection 24 between the openings 25–28 and the arms that connect the openings. Note that opening 46 is a square or rhombus with rounded corners. The gentle curvature from the narrow center to the wider ends of each arm causes the roundedness to the corners. Note also that the rounded corners are offset from the screw-receiving openings and from the overall rectangular shape of the subsection 24. This overall structure enables the arms to cooperate with their screw-receiving openings to give the cover flexibility. With this flexibility, the surgeon can conform the cover to the natural cranial surface.

The openings have the proper dimension for receiving a standard fastener to connect the cranial bone cover 10 to the patient's intact cranium 11. As FIGS. 2 and 4 show and focusing on opening 50 at the corner of plate 10, that opening includes successively a tapered recess 56 at the upper surface of the arms 52 and 54 and a cylindrical recess 58 at the arms' lower surfaces. The tapered and cylindrical recesses intersect at an interior lip 60. The recesses and lip are aligned along a common longitudinal axes 41. The dimensions of the recesses are such that a surgical bone screw passing partially through a screw-receiving opening secures that portion of the cover adjacent the screw-receiving opening to the remaining cranial bone. The recess allows the surgeon to counter-sink the screw so that its head does not project above the surface of the cover.

To use, the surgeon first removes the damaged or diseased bone and determines the size of the damage to the cranium. The surgeon then cuts part of the mesh 10 to become a properly-sized cover. Normally, he or she trims away extraneous material that would extend well beyond the damaged area. It is best if the trimming comes close to the outside openings as any arms that do not attach to two adjacent openings are extraneous. The remaining openings will lie on remaining bone that is strong enough to hold screws extending through the screw-receiving openings. The surgeon than fastens with bone screws those openings to the cranium.

Numerous modifications and alternate embodiments will occur to those skilled in the art. Therefore, applicant intends that the invention be limited only in terms of the appended claims.

I claim:

1. In a cover for covering a contoured surface comprising an array of generally evenly spaced screw-receiving openings, arms extending between the screw-receiving openings from one screw-receiving opening to the adjacent screw-receiving openings, each screw-receiving opening having a center and each arm having a centerline, the improvement comprising the provision of:

the space between the screw-receiving openings and the arms forming a rhombus having four rounded corners whose axes are offset to the common centerlines of the adjacent screw-receiving openings.

* * * * *